United States Patent [19]

Petty et al.

[11] Patent Number: 5,547,875
[45] Date of Patent: Aug. 20, 1996

[54] RECALIBRATING APPARATUS AND METHOD

[75] Inventors: John D. Petty, Holland Park; Russell M. Peachey, Durack, both of Australia

[73] Assignee: Ionode Pty Ltd., Queensland, Australia

[21] Appl. No.: 367,145

[22] PCT Filed: Jul. 16, 1993

[86] PCT No.: PCT/AU93/00356

§ 371 Date: Jan. 10, 1995

§ 102(e) Date: Jan. 10, 1995

[87] PCT Pub. No.: WO94/02945

PCT Pub. Date: Feb. 3, 1994

[30] Foreign Application Priority Data

Jul. 17, 1992 [AU] Australia ............... PL3588

[51] Int. Cl.⁶ .................................................. G01N 35/08
[52] U.S. Cl. .................. 436/8; 422/81; 422/82; 422/110; 422/115; 436/18; 436/52; 436/53; 436/179; 73/1 R; 73/1 G; 73/864.21; 73/864.22; 73/863.33
[58] Field of Search .............. 73/1 R, 1 G, 864.21, 73/864.22, 863.33; 422/81, 82, 100, 110, 115; 436/48, 49, 52, 53, 179, 8

[56] References Cited

U.S. PATENT DOCUMENTS

| | | | |
|---|---|---|---|
| 3,556,950 | 1/1971 | Dahms | 204/1 |
| 3,607,092 | 9/1971 | Neff | 422/81 |
| 3,630,088 | 12/1971 | Sawyer | 73/864.21 |
| 3,668,936 | 6/1972 | Herron | 73/423 A |
| 4,013,413 | 3/1977 | Stewart et al. | 422/81 |
| 4,333,356 | 6/1982 | Bartels et al. | 73/864.21 |
| 4,338,280 | 7/1982 | Ambers et al. | 73/864.22 |
| 4,341,107 | 7/1982 | Blair et al. | 73/3 |
| 4,441,374 | 4/1984 | Suzuki | 73/864.12 |
| 4,486,097 | 12/1984 | Riley | 356/410 |
| 4,490,236 | 12/1984 | Petty | 204/409 |
| 4,520,108 | 5/1985 | Yoshida et al. | 436/53 |
| 4,695,431 | 9/1987 | Farrell | 422/81 |
| 4,804,519 | 2/1989 | Sainz et al. | 422/81 |
| 5,080,866 | 1/1992 | Petty et al. | 422/80 |
| 5,157,957 | 10/1992 | Mettes et al. | 73/1 G |
| 5,185,263 | 2/1993 | Kronels et al. | 436/8 |
| 5,221,521 | 6/1993 | Hashizume et al. | 436/179 |
| 5,230,863 | 7/1993 | Salpeter | 422/81 |
| 5,239,856 | 8/1993 | Mettes et al. | 73/1 G |
| 5,254,313 | 10/1993 | Koroda et al. | 436/179 |

FOREIGN PATENT DOCUMENTS 0036171   9/1981   European Pat. Off. .

*Primary Examiner*—Jill Warden
*Assistant Examiner*—Sharidan Carrillo
*Attorney, Agent, or Firm*—Nixon & Vanderhye P.C.

[57] ABSTRACT

A method and apparatus for recalibrating analytical instruments such as atomic absorption and inductively coupled plasma spectrophotometers comprises the use of coupled piston pumps and valves in a fluid conduit system to obtain a sample value (h) during one half of a pump cycle and standard gradients (S1–S6) during the other half cycle. The piston pumps are actuated by cams of selected profiles to obtain a predetermined flow rate from each pump, the flow from each pump being selectively combined to construct standard gradients from two or more standard solutions and to effect autoranging of the standards in response to a previously determined sample value.

17 Claims, 2 Drawing Sheets

RECALIBRATING APPARATUS AND METHOD

BACKGROUND OF THE INVENTION

THIS INVENTION relates to the recalibration of sensors and instruments used for chemical analysis.

Flow based methods of analysis require periodic recalibration with standards. Generally, several external standards (typically between two to five depending on the characteristics of the sensor or instrument e.g. linear or non-linear) are measured at intervals between a group of samples, but in all periodic recalibrations, a compromise exists. Very frequent recalibration improves reliability, but at the expense of sample throughput. Infrequent recalibration increases the risk of an out of tolerance condition between recalibrations, requiring the sample measurements to be reworked.

U.S. Pat. No. 5,080,866 describes a cyclic flow based analytical technique (Discontinuous Flow Analysis) where the ratio of a reagent to sample is varied during the measurement half of the cycle, and one example of the technique shows how an internal recalibration can be performed with a single standard and stepped flow profile on every sample. This overcomes the problem of the frequency of recalibration inherent in the use of external standards. However, the concentration of the internal standard relative to the sample has to be within certain limits so that the accuracy of the recalibration is not impaired. If the sample and standard are close in concentration, the step changes are small, consequently the resolution may be insufficient for an accurate recalibration. If the sample and standard are considerably different in concentration, plateau responses for each step may not be achieved due to the detector response time, or diffusion effects.

It should be noted that in all cyclic analytical techniques which use piston pumps, the cycle for each pump comprises two complementary half-cycles: a forward stroke whereby fluid is expelled from the pump, and a return stroke whereby fluid is drawn into the pump. The measurement of the sample takes place during one of the half-cycles.

SUMMARY OF THE INVENTION

An object of the present invention is to provide a rapid, effective internal recalibration for fluid delivery systems, in particular, those employing a piston pump fluid delivery system in which recalibration requires a minimal number of standards, and which provides a recalibration between successive samples.

A further object of the present invention is to provide a recalibration system which can auto-range the recalibration to suit the preceding sample.

The present invention entails the realization that substantial benefits in line with these objectives can be achieved by utilizing a novel recalibration apparatus in which a reproducible recalibration profile between two standards is formed in the half cycle complementary to the sample measurement half cycle, and the measurement of the sample in the first half of the cycle is compared to the recalibration profile of the two standards in the second half of the cycle. Additional standards may be employed so that the recalibration can be auto-ranged to suit the preceding sample.

According to one aspect of the invention there is provided a recalibrating apparatus comprising:

a pump means for delivery of a fluid sample, reagent or sample/reagent mixture to a fluid junction;

first and second piston pump fluid delivery systems for delivery at first and second flow rates respectively of first and second fluid standards to the fluid junction;

conduit means providing fluid flow communication between the fluid junction and a sensor means;

mixing means to mix the first and second fluid standards upstream of the sensor means relative to a fluid flow direction;

sensor means responsive to a fluid condition of the fluid sample, reagent or sample/reagent mixture and responsive to a fluid condition in the first standard, said second standard or mixtures thereof;

flow rate control means operatively coupled to at least one of the first or second piston pump fluid delivery systems for controllably varying a flow rate thereof to produce a plurality of ratios of the first and second flow rates in accordance with a sequence of functional steps, each of which steps is defined by at least one of a distinct flow rate ratio, a series of distinct flow rate ratios, a distinct gradient of flow rate ratios, or a series of distinct gradients of flow rate ratios;

wherein the pump means and the first and second piston pump fluid delivery systems operate in reciprocal modes of a pumping cycle so that in one half cycle the pump means delivers the fluid sample, reagent or sample/reagent mixture to the sensor means while the first and second piston pump systems refill with first and second standards respectively, and in the other half cycle the first and second piston pump systems deliver the first and second fluid standard and mixtures thereof to the sensor means while the pump means reloads with sample or sample/reagent mixture;

and wherein the condition of the sample or sample/reagent mixture detected by the sensor is compared to the condition of the first and second fluid standards and/or mixtures thereof detected by the sensor to effect calibration of the sample.

The pump means for delivery of a fluid sample sample/reagent mixture may comprise a positive displacement pump.

Alternatively the pump means for delivery of a fluid sample or sample/reagent mixture may comprise a differential pumping means adapted to aspirate a sample and/or a sample/reagent mixture.

Suitably the mixing means is located in the conduit means between the fluid junction and the sensor means.

The recalibrating apparatus may comprise valves controlling respective ports associated with the first and second piston pumps and means for synchronizing the operation of the valves.

Preferably, the flow rate control means is adapted to produce substantially pulse free operation of the first and second piston pumps.

Suitably, the flow rate control means comprises cam means operatively associated with the first and second piston pumps.

Alternatively the flow rate control means may comprise an electrical or electro-mechanical control means such as a linear actuation device or stepping motor operatively associated with the first and second piston pumps.

If required, the recalibrating apparatus may include one or more additional piston pump means for delivery of a further fluid standard to the fluid junction.

The recalibrating apparatus may include electronic control means to selectively actuate valves associated with the first, second or additional piston pump means, the electronic control means being operatively coupled to the sensor means to effect, in use, autoranging of fluid standards associated with the first, second and additional piston pump means.

If required the sensor means may vaporise the sample or sample/reagent mixture.

Suitably the sensor means comprises an atomic absorption spectrophotometer or an inductively coupled plasma spectrophotometer.

According to a further aspect of the invention there is provided a method of recalibrating a chemical analysis apparatus, the method comprising the steps of:

delivering a fluid sample or sample/reagent mixture via a fluid junction to a sensor means responsive to a fluid condition of the sample or sample/reagent during a first half of an operational cycle;

delivering first and second fluid standards and mixtures thereof via the fluid junction to the sensor means during a second half of an operational cycle;

controllably varying at least one of a flow rate of the first and second fluid standards to produce a plurality of ratios of the flow rates of the first and second fluid standards in accordance with a sequence of functional steps each of which is defined by at least one of a distinct flow rate ratios, a distinct gradient of flow rate ratios, or a series of distinct gradients of flow rate ratios;

mixing the first and second fluid standards upstream of the sensor means relative to a direction of fluid flow through the sensor means;

sensing a fluid condition of the sample or sample/reagent mixture arriving at said sensor means during the first half cycle and subsequently sensing a fluid condition of the first and second fluid standards and mixtures thereof to effect analysis of the sample or sample/reagent mixture;

wherein the analysis is determined by the relationship between the sensed condition of the fluid sample or sample/reagent mixture and the sensed condition of the first and second fluid standards and mixtures thereof.

If required delivery of the fluid sample or sample/reagent mixture may be effected by positively pumping the fluid sample or sample/reagent to the sensor means.

Alternatively delivery of the fluid sample or sample/reagent mixture to the sensor means may be effected by aspiration of the fluid sample or sample/reagent mixture with differential pumping means.

The the sequence of functional steps may include sequentially a distinct flow rate of the first fluid standard, a distinct gradient of flow rate ratios between the first and second fluid standards, and a distinct flow rate of the second standard.

Alternatively, the sequence of functional steps may include sequentially, a distinct flow rate of the first fluid standard, a series of distinct flow rate ratios between the first and second fluid standards, and a distinct flow rate of the second fluid standard.

Suitably, the fluid condition of the sample or sample/reagent mixture in the first half cycle is compared to a recalibration profile constructed from sensed fluid conditions of the first and second fluid standards and mixtures thereof, the recalibration profile being constructed during the second half cycle.

If required, one or more additional fluid standards may be selectively introduced into the sensor means during the second half cycle to effect autoranging of the fluid standards.

According to yet another aspect of the invention there is provided a fluid flow chemical analysis apparatus comprising a recalibration apparatus according to a first aspect of the invention.

BRIEF DESCRIPTION OF THE DRAWINGS

In order that the invention may be clearly understood and readily carried into effect, preferred embodiments and exemplary methods of operation, will now be described with reference to the accompanying drawings, in which.

DETAILED DESCRIPTION OF PREFERRED EMBODIMENTS

Figure 1:
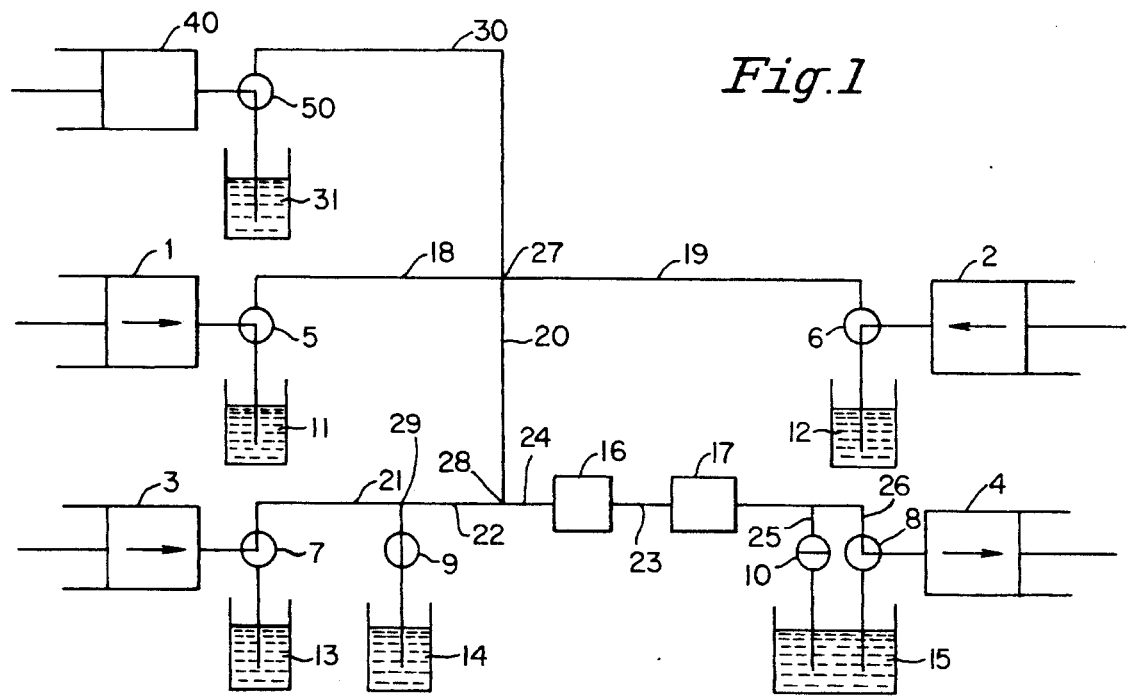
FIG. 1 is a combination block diagram of a configuration of recalibrating apparatus for carrying out the method of the invention where differential pumping is used to aspirate the sample in the sample measurement half-cycle.

Referring to FIG. 1, during the sample measurement half-cycle, positive piston pump 3 urges reagent 13 through three-way valve 7 and along conduit 21 towards T-junction 29. Simultaneously, suction pump 4 draws fluid from T-junction 29 through conduits 22 and 24, via mixer 16 to conduit 23 and via sensor 17 to conduit 26 and then into suction pump 4 via three way valve 8.

The differences in flow rates between positive pump 3 and suction pump 4 determine the flow rate or rates of sample 14 aspirated towards T-junction 29.

Any flow program comprising a sequence of functional steps, each of defined flow rate ratio or ratios, may be chosen in accordance with the principles described in our U.S. Pat. No. 5,080,866, for example fixed ratios or gradients.

In the sample measurement half-cycle, two-way valve 9 is open to the sample, and two-way valve 10 is closed to waste 15. As well, three-way valves 5 and 6 are closed to conduits 18, 19 and 20 so that piston pumps 1 and 2 refill with standards 11 and 12 respectively.

The second (recalibration) half of the cycle commences with valves 5,6,7,8,9 and 10 reversing their states, that is, three-way valves 5 and 6 are open to conduits 18, 19 and 20; three-way valves 7 and 8 are closed to conduits 21, 22, 23, 24 and 26; two-way valve 9 is closed to sample 14, and two-way valve 10 is opened to waste 15.

Simultaneously, piston pump 1 directs standard 11 through three-way valve 5 and along conduit 18 towards junction 27, while piston pump 2 directs standard 12 through three-way valve 6 and along conduit 19 towards junction 27. Standards 11 and 12 combine at junction 27 and the combined stream flows along conduits 20 and 24; past mixer 16 and along conduit 23; past sensor 17 and along conduit 25; and through two-way valve 10 to waste 15.

The ratio of the flow rates of pumps 1 and 2 through the recalibration half-cycle can be a distinct flow ratio, a series of distinct flow ratios, a distinct gradient of flow rate ratios, or a series of distinct gradients of flow rate ratios or any combination thereof. During the calibration half-cycle, piston pump 3 refills with reagent 13 through three-way valve 7 while suction pump 4 discharges to waste 15 through three-way valve 8.

Standard 11 may be replaced by standard 31 to effect auto-ranging, that is, the recalibration profile is altered by maintaining three-way valve 5 closed during the recalibration half-cycle, and opening three-way valve 50 so that standard 31 travels along conduit 30 to join standard 12 at junction 27. Mixer 16 should preferably be a low volume, low dispersion type as described in our U.S. Pat. No. 5,040,898. The piston pumps may be driven by any means capable of producing the required piston movement, for example, stepper motors, cams with selected profiles, servo controls, or the like.

Figure 2:
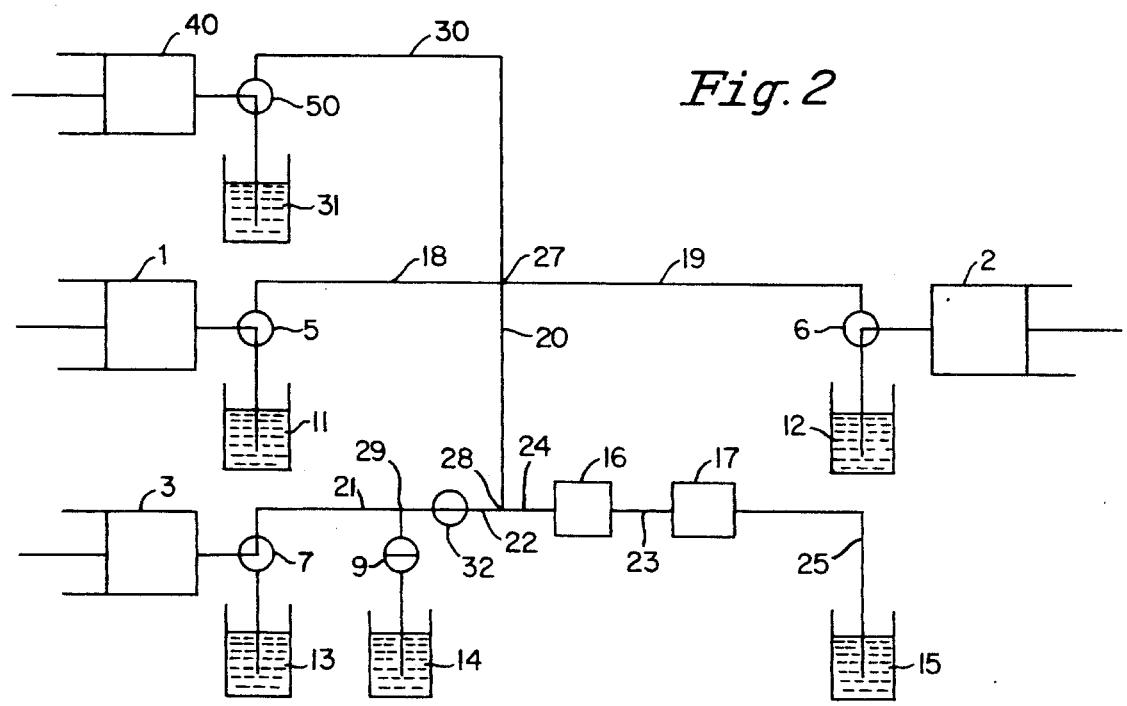
FIG. 2 is a combination block diagram of a configuration of recalibrating apparatus for carrying out the method of the invention where positive pumping only to the sample and/or sample reagent mixtures is used in the sample measurement half-cycle.

In FIG. 2, the function of pumps 1,2 and 40 is the same as in FIG. 1, but the sample measurement half-cycle involves positive pumping of the sample by piston pump 3 rather than aspiration by a differential pumping means. With two-way valve 32 closing conduit 22 and two-way valve 9 open, sample 14 is drawn along conduit 21 while recalibration is taking place. During the sample measurement half-cycle, two-way valve 9 is closed to sample 14 and two-way valve 32 opens conduit 22, so that sample 14 is urged along conduit 24, through mixer 16; along conduit 23 and through sensor 17; and along conduit 25 to waste 15.

Figure 3:
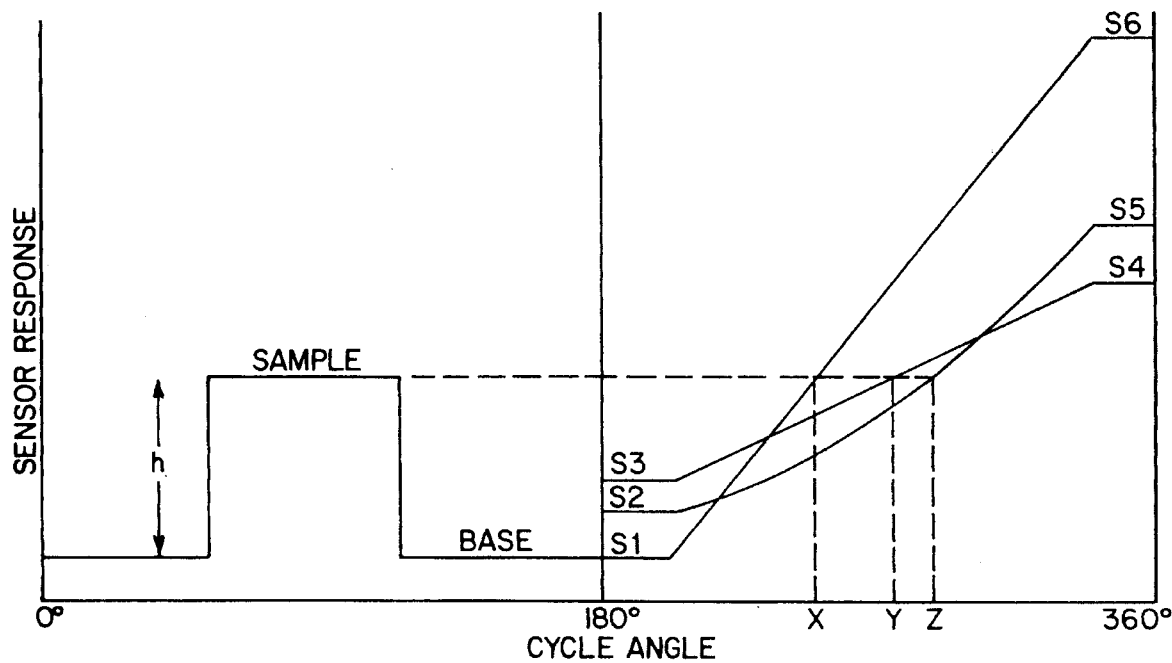
FIG. 3 shows schematically a sensor response to a sample and three standard calibration curves.

FIG. 3 shows schematically a sensor response to a sample in the first half of a pump cycle (0°–180°) and three standard gradient calibration curves in the second half of the cycle (180°–360°).

The sample response rises from a base line to a plateau value "h" and then returns to the base line.

Curve S1-S6 represents a typical linear gradient calibration for standards S1 and S6 with plateau regions for those standards on each side of the curve.

Curve S3-S4 represents a narrow range linear gradient calibration for standards S3 and S4, again with plateau responses corresponding to each individual standard. This narrow range gradient closely "brackets" the sample response value to obtain a higher degree of accuracy.

Accordingly, it can be seen that by employing an appropriate range of standards for calibration purposes, the apparatus and method of the invention permit autoranging of the calibration half cycle by selecting particular standards on the basis of the sample response value detected in the preceding half cycle.

The calibration gradient between standards S2 and S5 demonstrates a non-linear calibration. The sample value is determined by extrapolation of the sample response value (h) across to the appropriate calibration curve. The intersection point (X, Y or Z) as measured by cycle angle (eg. encoder pulses) is a function of sample concentration.

Figure 4:
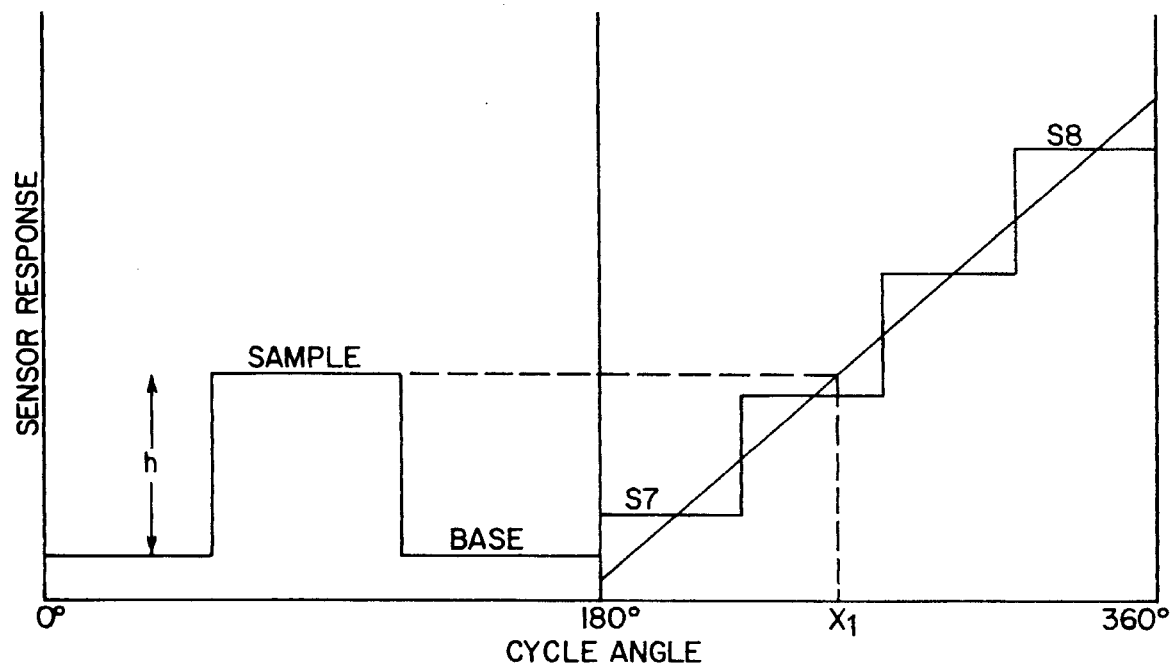
FIG. 4 shows schematically a sensor response to a sample and a stepped calibration curve.

FIG. 4 illustrates schematically a step profile calibration curve in which the plateau response values of standards S7, S8 and mixtures thereof are employed to construct a calibration curve with a linear gradient.

As with the calibration curves shown in FIG. 3, the sample response value is extrapolated to the calibration curve where the intersection point ($X_1$) is measured by cycle angle, is a function of simple concentration.

From experiments conducted with a flame atomic absorption spectrophotometer, the method of stepped standard additions, illustrated by FIG. 4, produces highly repeatable quantitative analyses. The particular advantages which were noted included:

(a) Marked reduction in manual preparation of solutions.

(b) Continuous recalibration of the instrument.

(c) Continual monitoring of instrumental drift.

(d) Monitoring of matrix effects, both chemical and physical.

(e) Automation of the method of standard additions.

(f) Good repeatability.

(g) Ready accumulation of quality assurance data.

(h) Maintenance of high throughput, despite a marginally longer run time, as each pump cycle produces a working curve and analytical measurement. Unproductive measurements such as calibration and check standards are eliminated.

The classical application of the sample bracketing method illustrated by FIG. 3 involves several measurements and standard preparations for each sample and is usually too laborious and time consuming for use in production analyses. Experimental data produced with the arrangement of FIG. 2 using a flame atomic absorption spectrophotometer as the sensor means (17) have produced analyses which are highly repeatable (<1% RSD) and show good accuracy for known samples.

The method and apparatus according to the invention permit a significant increase in productive analysis time and a reduction in the time required to prepare standards yet without any compromise to accuracy and repeatability of analytical measurements. Moreover, methods such as standard additions and sample bracketing, previously rejected in favor of more cost effective compromises, have now become automated and routine by virtue of the present invention.

It will be readily apparent to a skilled addressee that many modifications and variations may be made to the present invention without departing from the spirit and scope thereof.

We claim:

1. A recalibrating apparatus comprising:

pump means for delivery of a fluid sample, reagent or sample/reagent mixture to a fluid junction;

first and second piston pump fluid delivery systems for delivery at first and second flow rates respectively of first and second fluid standards to said fluid junction;

conduit means providing fluid flow communication between said fluid junction and sensor means;

mixing means to mix said first and second fluid standards upstream of said sensor means relative to a fluid flow direction;

sensor means responsive to a fluid condition of said fluid sample, reagent or sample/reagent mixture and responsive to a fluid condition in said first standard, said second standard or mixtures thereof;

flow rate control means operatively coupled to at least one of said first or second piston pump fluid delivery systems for controllably varying a flow rate thereof to produce a plurality of ratios of said first and second flow rates in accordance with a sequence of functional steps, each of which steps is defined by at least one of a distinct flow rate ratio, a series of distinct flow rate ratios, a distinct gradient of flow rate ratios, or a series of distinct gradients of flow rate ratios;

said flow rate control means operatively coupled to said pump means and said first and second piston pump fluid delivery systems for operating said pump means and said first and second delivery systems in reciprocal modes of a pumping cycle so that in one half cycle said pump means delivers said fluid sample, reagent or sample/reagent mixture to said sensor means while said first and second piston pump systems refill with first and second standards respectively, and in the other half cycle said first and second piston pump systems deliver said first and second fluid standard and mixtures thereof to said sensor means while said pump means reloads with sample or sample/reagent mixture;

and wherein the condition of said sample or sample/reagent mixture detected by said sensor is compared to the condition of said first and second fluid standards and/or mixtures thereof detected by said sensor to effect calibration of said sample.

2. An apparatus as claimed in claim 1 wherein the pump means for delivery of a fluid sample or sample/reagent mixture comprises a positive displacement pump.

3. An apparatus as claimed in claim 1 wherein the pump means for delivery of a fluid sample or sample/reagent mixture comprises a differential pumping means adapted to aspirate a sample and/or a sample/reagent mixture.

4. An apparatus as claimed in claim 1 wherein said mixing means is located in said conduit means between said fluid junction and said sensor means.

5. An apparatus as claimed in claim 1 wherein said flow rate control means is adapted to produce substantially pulse free operation of said first and second piston pumps.

6. An apparatus as claimed in claim 5 wherein said flow rate control means comprises cam means operatively associated with said first and second piston pumps.

7. An apparatus as claimed in claim 5 wherein said flow rate control means comprises a linear actuation device or stepping motor operatively associated with said first and second piston pumps.

8. An apparatus as claimed in claim 1 including one or more additional piston pump means for delivery of a further fluid standard to said fluid junction.

9. An apparatus as claimed in claim 8 including electronic control means to selectively actuate valves associated with said first, second or additional piston pump means, said electronic control means being operatively coupled to said sensor means to effect, in use, autoranging of fluid standards associated with said first, second and additional piston pump means.

10. An apparatus as claimed in claim 1 wherein the sensor means vaporises the sample or sample/reagent mixture.

11. An apparatus as claimed in claim 1 wherein the sensor means comprises an atomic absorption spectrophotometer or an inductively coupled plasma spectrophotometer.

12. A method of recalibrating a chemical analysis apparatus, said method comprising the steps of:

delivering a fluid sample or sample/reagent mixture via a fluid junction to sensor means responsive to a fluid condition of said sample or sample/reagent during a first half of an operational cycle;

delivering first and second fluid standards and mixtures thereof via said fluid junction to said sensor means during a second half of an operational cycle to produce a recalibration profile;

controllably varying at least one of a flow rate of said first and second fluid standards during said second half of the operational cycle to produce a plurality of ratios of said flow rates of said first and second fluid standards in accordance with a sequence of functional steps each of which is defined by at least one of a distinct flow rate ratio, a distinct gradient of flow rate ratios, or a series of distinct gradients of flow rate ratios;

mixing said first and second fluid standards upstream of said sensor means relative to a direction of fluid flow through said sensor means during said second half of the operational cycle;

sensing a fluid condition of said sample or sample/reagent mixture arriving at said sensor means during said first half cycle and subsequently sensing a fluid condition of said first and second fluid standards and mixtures thereof during the second half of the operational cycle;

wherein the fluid condition of the sample or sample/reagent mixture in the first half cycle is compared to the recalibration profile constructed from sensed fluid conditions of the first and second fluid standards and mixtures thereof, said recalibration profile being constructed during said second half cycle.

13. A method as claimed in claim 12 wherein delivery of said fluid sample or sample/reagent mixture may be effected by positively pumping said fluid sample or sample/reagent to said sensor means.

14. A method as claimed in claim 12 wherein delivery of said fluid sample or sample/reagent mixture to said sensor means may be effected by aspiration of said fluid sample or sample/reagent mixture with differential pumping means.

15. A method as claimed in claim 12 wherein said sequence of functional steps may include sequentially a distinct flow rate of said first fluid standard, a distinct gradient of flow rate ratios between said first and second fluid standards, and a distinct flow rate of said second standard.

16. A method as claimed in claim 12 wherein said sequence of functional steps may include sequentially, a distinct flow rate of said first fluid standard, a series of distinct flow rate ratios between said first and second fluid standards, and a distinct flow rate of said second fluid standard.

17. A method as claimed in claim 1 wherein one or more additional fluid standards is selectively introduced into said sensor means during said second half cycle to effect autoranging of said fluid standards.

\* \* \* \* \*